(12) United States Patent
Lucas et al.

(10) Patent No.: US 9,833,365 B2
(45) Date of Patent: Dec. 5, 2017

(54) BREAST WRAP

(71) Applicant: MUMDROP HOLDINGS LIMITED, Papakura (NZ)

(72) Inventors: Jennifer Lucas, Papakura (NZ); Philippa de Vere, Tauranga (NZ)

(73) Assignee: MUMDROP HOLDINGS LIMITED, Karaka (NZ)

( * ) Notice: Subject to any disclaimer, the term of this patent is extended or adjusted under 35 U.S.C. 154(b) by 293 days.

(21) Appl. No.: 14/372,457

(22) PCT Filed: Jan. 18, 2013

(86) PCT No.: PCT/NZ2013/000003
§ 371 (c)(1),
(2) Date: Jul. 16, 2014

(87) PCT Pub. No.: WO2014/007653
PCT Pub. Date: Jan. 9, 2014

(65) Prior Publication Data
US 2014/0378933 A1 Dec. 25, 2014

(30) Foreign Application Priority Data

Jan. 18, 2012 (NZ) .......................................... 597683
Sep. 7, 2012 (NZ) .......................................... 602329

(51) Int. Cl.
*A61F 13/15* (2006.01)
*A61F 13/20* (2006.01)
(Continued)

(52) U.S. Cl.
CPC .............. *A61F 13/45* (2013.01); *A61F 13/14* (2013.01); *A61F 13/141* (2013.01);
(Continued)

(58) Field of Classification Search
CPC ........ A61F 13/14; A61F 13/141; A61F 13/45; A61F 13/56; A61F 2013/15016
See application file for complete search history.

(56) References Cited

U.S. PATENT DOCUMENTS 2,723,396 A * 11/1955 Stack ........................ A61F 5/03
450/58
3,189,028 A * 6/1965 Dormire ................... A41C 3/06
128/DIG. 15
(Continued)

FOREIGN PATENT DOCUMENTS

CN 2179007 Y 10/1994
CN 2396796 Y 9/2000
(Continued)

*Primary Examiner* — Michele M Kidwell
(74) *Attorney, Agent, or Firm* — Greer, Burns & Crain, Ltd.

(57) ABSTRACT

The invention relates to a breast wrap for absorbing fluid secreted from a wearer's breasts. In one embodiment the breast wrap comprises a panel of material, means for fastening the panel in a continuous band, one or more absorbent regions on a first side of the panel, and first and second adjustment means independently operable to adjust the tightness of the band along first and second adjustment regions proximate the top and bottom of the band respectively. In use, the wrap is configured to wrap around a wearer's chest and substantially cover the wearer's breasts with the one or more absorbent regions covering the wearer's nipples and the first and second adjustment regions positioned above and below the wearer's breasts respectively. In another embodiment, the breast wrap comprises one or more absorbent panels removably attached to a first side of the first panel and, in use, the one or more absorbent panels cover the wearer's nipples.

9 Claims, 10 Drawing Sheets

(51) Int. Cl.
*A61F 13/45* (2006.01)
*A61F 13/14* (2006.01)
*A61F 13/537* (2006.01)
*A61F 13/56* (2006.01)
*A61F 13/53* (2006.01)

(52) U.S. Cl.
CPC ........ *A61F 13/53708* (2013.01); *A61F 13/56* (2013.01); *A61F 2013/15016* (2013.01); *A61F 2013/530029* (2013.01); *A61F 2013/530343* (2013.01)

(56) References Cited

U.S. PATENT DOCUMENTS

| | | | | |
|---|---|---|---|---|
| 3,529,601 | A | * | 9/1970 | Kirkland .................. A61F 5/03 601/1 |
| 3,970,079 | A | * | 7/1976 | Gaylord, Jr. .......... A61F 13/143 156/157 |
| 4,527,566 | A | * | 7/1985 | Abare ....................... A61F 7/02 601/15 |
| 4,676,247 | A | * | 6/1987 | Van Cleve ................ A61F 7/02 607/112 |
| 4,738,745 | A | | 4/1988 | Fukuzaki et al. |
| 4,960,112 | A | * | 10/1990 | Anderegg ............. A61F 13/141 2/118 |
| 5,060,648 | A | * | 10/1991 | Zarkesh .................... A61F 7/10 450/79 |
| 5,427,563 | A | | 6/1995 | Manning |
| 5,429,593 | A | * | 7/1995 | Matory .................. A61F 13/145 2/114 |
| 5,871,388 | A | * | 2/1999 | Lambert .................... A41C 3/02 2/73 |
| 6,015,331 | A | | 1/2000 | Ioakim |
| 7,775,851 | B2 | | 8/2010 | Sgro |
| 7,776,019 | B2 | | 8/2010 | Kawakami et al. |
| 8,142,255 | B2 | | 3/2012 | Johnston |
| 2004/0058619 | A1 | | 3/2004 | Spiezio et al. |
| 2004/0224605 | A1 | | 11/2004 | Cano Chabolla |
| 2007/0099542 | A1 | | 5/2007 | Sakaguchi et al. |
| 2007/0287977 | A1 | | 12/2007 | Fujikawa et al. |
| 2009/0004950 | A1 | | 1/2009 | Sgro |
| 2009/0131900 | A1 | | 5/2009 | Tsutsui et al. |
| 2012/0142253 | A1 | * | 6/2012 | Javaid ..................... A41C 3/04 450/80 |

FOREIGN PATENT DOCUMENTS

| | | |
|---|---|---|
| EP | 1125511 A1 | 8/2001 |
| GB | 2445725 A | 7/2008 |
| JP | 2000239903 A | 9/2000 |
| JP | 2003013305 A | 1/2003 |
| TW | I265791 B | 11/2006 |

\* cited by examiner

BREAST WRAP

CROSS REFERENCE TO RELATED APPLICATIONS

This application claims the benefit of and priority to New Zealand Application No. 597683 filed on Jan. 1, 2012, and New Zealand Application No. 602329 filed on Sep. 7, 2012, the entirety of which are incorporated by reference herein.

FIELD OF INVENTION

The invention relates to a breast wrap for absorbing fluid secreted from a wearer's breasts.

BACKGROUND

The milk ejection reflex or let-down reflex occurs in breastfeeding mothers to trigger lactation of milk from the breast. A suckling baby typically initiates the reflex but there are other causes, such as the sound of a baby crying or a warm sensation on the breast or chest. The latter may cause some women to lactate during and after a shower.

Undesirable lactation can be annoying, inconvenient, messy and sometimes embarrassing. In the case of lactation that continues after a shower, it can be difficult for the woman to dry herself, get dressed and perform other personal grooming acts until the lactation has stopped, which may take some time. The motion of bending over during drying and dressing may also cause or exacerbate lactation.

The usual way women deal with this situation is to wrap a towel around themselves. However, if one hand is needed to keep the towel in place, drying and dressing is difficult. Tucking the towel into itself keeps two hands free but the towel can easily come loose or undone, thus removing pressure from the breast that is desirable to slow down the milk ejection reflex. In addition, a towel does not provide any support underneath the breasts, which can be uncomfortable, particularly when the breasts are engorged or tender. Towel wraps are also known which use VELCRO®, hook-and-loop fastening material, to hold them in place but they also possess the aforementioned disadvantages.

U.S. Pat. No. 7,775,851 discloses a fabric breast support designed to be worn by pregnant women or breastfeeding mothers in the shower to support and soothe the breasts, as well as shield them from contact with potentially painful or irritating water sprays or chemical toiletries. The breast support in this document has some degree of absorbency but is not intended to be used as a towel. It is attached around the body by connecting two pads of VELCRO®, hook-and-loop fastening material, to one another. This arrangement provides little flexibility to accommodate women of different shapes and sizes, and results in pressure being applied around the middle of the garment, which is usually positioned across the nipples and may therefore be sore for the wearer.

Lactating women may also find discharge in bed a problem because of the volume of moisture that can be produced and the uncomfortable feeling caused by damp bedclothes or sheets. Many women use reusable or disposable breast pads inside a bra or tight top to absorb the leakage but the pads can easily slip out of place and lose their efficacy.

It is an object of the invention to provide an improved breast wrap that addresses one or more of the foregoing disadvantages or to at least provide the public with a useful choice.

SUMMARY

According to a first aspect of the invention, there is provided a breast wrap comprising:
a panel of material;
means for fastening the panel in a continuous band;
one or more absorbent regions on a first side of the panel; and
first and second adjustment means independently operable to adjust the tightness of the band along first and second adjustment regions proximate the top and bottom of the band respectively,
wherein, in use, the wrap is configured to wrap around a wearer's chest and substantially cover the wearer's breasts with the one or more absorbent regions covering the wearer's nipples and the first and second adjustment regions positioned above and below the wearer's breasts respectively.

Preferably, the wrap comprises an elastic region along the bottom of the panel. The term "elastic" will be understood to describe any material tending to resume or return to its original shape after deformation, examples of which are the cords, tapes and fabrics that exhibit elastic behaviour commonly used in clothing.

Preferably, the first and/or second adjustment means comprises the means for fastening the panel.

More preferably, the means for fastening the panel comprises at least one set of co-operating fastening members. Each set of co-operating fastening members may comprise at least one first fastening member proximate a first end of the panel and at least one second fastening member proximate the second end of the panel, the first and second fastening members able to fasten together in different configurations, thereby allowing the tightness of the band to be adjusted along the first and second adjustment regions.

In one embodiment, the sets of co-operating fastening members comprise co-operating hook-and-loop fastener portions.

Preferably, at least one fastening member of each set of co-operating fastening members is elongate such that the sets of co-operating fastening members can be fastened together in a plurality of positions corresponding to different degrees of tightness of the band.

Preferably, the panel comprises a first end having a sloped edge, the bottom of the panel extending further than the top of the panel.

Preferably, the panel comprises a second end having a taper along the bottom of the panel.

In preferred embodiments of the invention, the wrap comprises fastening members attached to the panel in any or all of the following positions:
1. Proximate the corner of the panel where the sloped edge of the first end meets the bottom of the panel;
2. Proximate the corner of the panel where the sloped edge of the first end meets the top of the panel;
3. Proximate the corner of the panel where the taper along the bottom of the panel begins; and
4. Proximate the top of the panel, proximate the second end of the panel.

The wrap may comprise an elastic region along the sloped edge of the first end of the panel.

Preferably, the panel includes one or more darts extending upwards from the bottom of the first panel. The darts may help to breast wrap fit comfortably around the wearer's body.

In some embodiments of the invention, the panel of material comprises an absorbent layer and a visually appealing layer, the absorbent layer positioned to face inwards towards the wearer in use.

In a second aspect, the invention relates to the use of a breast wrap according to the first aspect of the invention for wrapping around a wearer's breasts.

Preferably, the use of the breast wrap comprises absorbing fluid secreted from the wearer's breasts.

Preferably, the use of the breast wrap comprises wrapping around a wearer's breasts after a bath, shower or the like.

A third aspect of the invention relates to a method of manufacturing a breast wrap comprising:

providing a panel of material having one or more absorbent regions on a first side;

attaching one or more means for fastening to the panel such that the panel is able to be fastened in a continuous band;

providing the panel with first and second adjustment means independently operable to adjust the tightness of the band along first and second adjustment regions proximate the top and bottom of the band respectively, wherein the first and second adjustment means are provided such that, when the wrap is wrapped around a wearer's chest to substantially cover the wearer's breasts, the one or more absorbent regions cover the wearer's nipples and the first and second adjustment regions are positioned above and below the wearer's breasts respectively.

Preferably, the method comprises providing an elastic region along the bottom of the panel.

Preferably, the method comprises forming a sloped edge in a first end of the panel such that the bottom of the panel extends further than the top of the panel.

In preferred embodiments of the invention, the step of attaching one or more means for fastening to the panel comprises attaching fastening members to the panel in any or all of the following positions:

1. Proximate the corner of the panel where the sloped edge of the first end meets the bottom of the panel;
2. Proximate the corner of the panel where the sloped edge of the first end meets the top of the panel;
3. Proximate the bottom edge of the first panel at one or more locations along the edge; and
4. Proximate the top of the panel, proximate or near the second end of the panel.

More preferably, the method comprises forming an elastic region along the sloped edge of the first end of the panel.

In some embodiments of the invention, the method comprises forming the panel of material from an absorbent layer and a visually appealing layer, the absorbent layer positioned to face inwards towards the wearer in use.

In a fourth aspect of the invention, there is provided a pattern for a panel of material suitable for forming part of a breast wrap in accordance with the first aspect of the invention together with instructions for forming the breast wrap using the method of the third aspect of the invention.

According to a fifth aspect of the invention, there is provided a breast wrap comprising:

a first panel of material;
means for fastening the first panel in a continuous band; and
one or more absorbent panels removably attached to a first side of the first panel,
wherein, in use, the wrap is configured to wrap around a wearer's chest and substantially cover the wearer's breasts with the one or more absorbent panels covering the wearer's nipples.

Preferably, the absorbent panel comprises at least one layer of absorbent material. More preferably, the absorbent material(s) may be any one or more of: cotton, chamois or bamboo terry cloth, velour or towelling material, or an absorbent microfibre. The absorbent layer(s) acts to absorb moisture secreted by the wearer's nipples.

In some embodiments, the absorbent panel comprises two or more layers of absorbent material. For example, the absorbent panel may comprise a layer of bamboo towelling and a layer of absorbent microfibre.

Preferably, the absorbent panel comprises a layer of moisture wicking material. It will be understood that moisture wicking material is material that is able to transmit moisture, for example by capillary action. For example, the moisture wicking material may be microfleece, polar fleece, suedecloth or microchamois. In some embodiments, the absorbent panel is configured such that, in use, the layer of moisture wicking material is positioned closer to the wearer's skin than the layer of absorbent material. The moisture wicking layer may help to transmit moisture away from the skin and increase comfort.

In some embodiments, the absorbent panel comprises a layer of waterproof or water resistant material, for example, polyurethane laminated polyester (PUL). The absorbent panel may be configured such that, in use, the layer of waterproof material is the absorbent panel layer positioned further from the wearer's skin than the layer of absorbent material. The waterproof layer may help to reduce moisture leaking away from the breast wrap.

Preferably, the absorbent panel is removably attached to a first end of the first panel of material. The first end of the first panel of material may, in use, be configured to be placed across the wearer's chest with a second end of the first panel of material configured to overlap and fasten to the first end to form the continuous band.

In preferred embodiments, the breast wrap comprises one or more absorbent panel fastening members for removably attaching the absorbent panel to the first panel of material. For example, the breast wrap may comprise two or four sets of absorbent panel fastening members for attaching portions of the absorbent panel proximate to corners of the absorbent panel to the first panel of material.

Preferably, the breast wrap comprises a breast wrap according to the first aspect of the invention.

In a sixth aspect, the invention relates to the use of a breast wrap according to the first aspect of the invention for wrapping around a wearer's breasts.

Preferably, the use of the breast wrap comprises absorbing fluid secreted from the wearer's breasts.

Preferably, the use of the breast wrap comprises wrapping around a wearer's breasts when the wearer is in bed.

Preferably, the use of the breast wrap comprises wrapping around a wearer's breasts after a bath, shower or the like.

According to a seventh aspect of the invention there is provided a method of manufacturing a breast wrap comprising:

providing a first panel of material;
attaching one or more means for fastening to the first panel such that the panel is able to be fastened in a continuous band;
attaching, in a removable manner, one or more absorbent panels to a first side of the first panel of material in a position such that, when the wrap is wrapped around a wearer's chest to substantially cover the wearer's breasts, the one or more absorbent panels cover the wearer's nipples.

Preferably, the method comprises forming the absorbent panel by attaching together one or more layers of absorbent material with one or more of the following:
1. A layer of moisture wicking material; and
2. A layer of waterproof or water resistant material.

Preferably, the method comprises mounting one or more absorbent panel fastening members to the absorbent panel and/or the first panel of material. More preferably, the method comprises mounting co-operating portions of a plurality of sets of absorbent panel fastening members to the absorbent panel and the first panel of material respectively.

Preferably, the method further comprises a method of manufacturing a breast wrap according to the third aspect of the invention.

In a further aspect of the invention, there is provided a pattern for a first panel of material and at least one absorbent panel suitable for forming part of a breast wrap in accordance with the first aspect of the invention together with instructions for forming the breast wrap using the method of the third aspect of the invention.

According to an eighth aspect of the invention, there is provided an absorbent panel for a breast wrap, the absorbent panel comprising:
  at least one layer of absorbent material; and
  means for fastening the absorbent panel to the breast wrap.

Preferably, the absorbent panel further comprises a layer of moisture wicking material attached to the layer(s) of absorbent material. The absorbent panel may be configured such that, when attached to the breast wrap, the layer of moisture wicking material is further from the breast wrap than the layer of absorbent material.

In further preferred embodiments, the absorbent panel comprises a layer of waterproof or water resistant material attached to the layer(s) of absorbent material. The absorbent panel may be configured such that, when attached to the breast wrap, the layer of waterproof material is closer to the breast wrap than the layer of absorbent material.

Preferably, the absorbent panel includes a first layer of moisture wicking material, two layers of absorbent material and a layer of waterproof or water resistant material.

Preferably, the means for fastening comprises one or more fastening members. The fastening members may be parts of sets of fastening members, the co-operating parts of the sets being fastened to the breast wrap and configured to receive the parts of the sets on the absorbent panel. More preferably, the fastening members are positioned in each corner of the absorbent panel.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION

Figure 1:
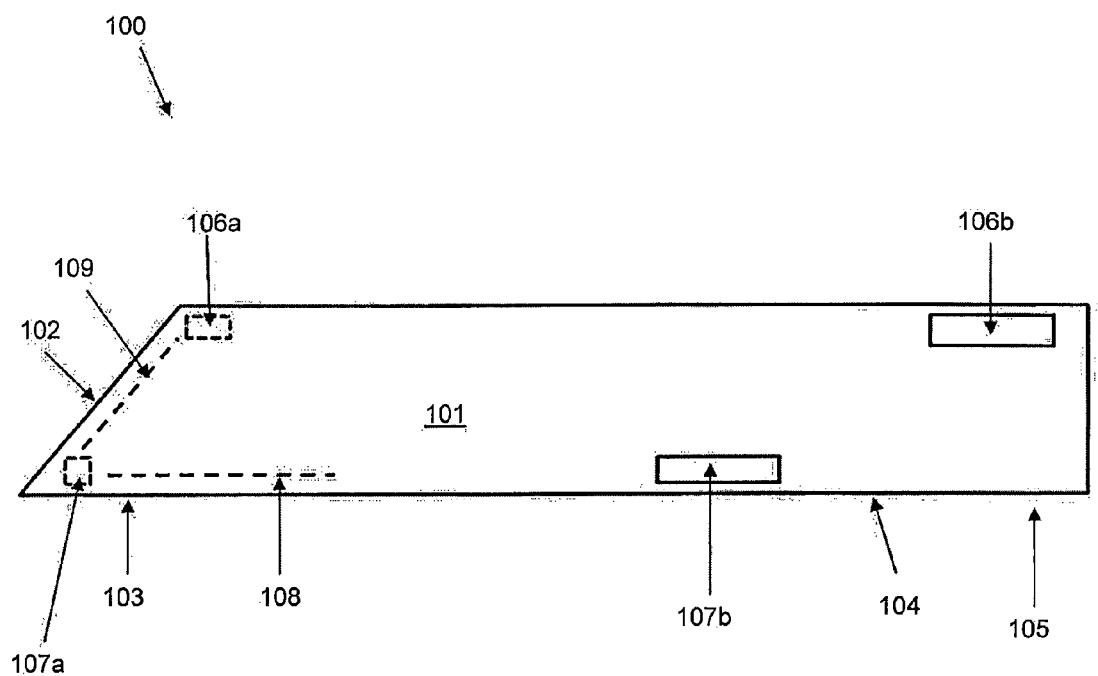
FIG. 1 is a plan view illustration of a breast wrap according to an embodiment of the invention.

FIG. 1 is a plan view illustration of a breast wrap 100 according to an embodiment of the invention. Breast wrap 100 is shown in its unwrapped state. In use, breast wrap 100 is wrapped around a wearer's body and fastened into a band. The breast wrap is able to be wrapped around a wearer's chests to cover the wearer's breasts and thereby absorb fluids being secreted from the breasts and in particular the nipples. As will be described, the breast wrap has a number of features that particularly suit it to this purpose.

Breast wrap 100 comprises a panel of material 101. The panel of material may be any size or shape suitable for being able to be wrapped around a wearer's breasts. However, in the preferred embodiment shown in FIG. 1, the panel of material 101 is elongate in shape with a sloped edge 102 at a first end 103, the slope being such that the bottom of the panel extends further than the top of the panel, and a bottom edge 104 at a second end 105 of the panel. This shape allows the breast wrap to sit comfortably around a wearer's breasts without excess material and permits adjustment of the wrap to fit different shapes and sizes of wearers, as will be described further below.

Features such as darts or pleats may be incorporated into the panel to improve the fit of the breast wrap around the wearer, improving comfort and style. If included, darts may be located along bottom edge 104 of the panel 101. In one possible embodiment, panel 101 includes three darts, at least two of them substantially corresponding to the approximate position of the breasts when the wrap is being worn.

Panel 101 may comprise a single piece of material or it may be comprised of a plurality of pieces of material joined together. Using a single piece of material avoids the need to join more than one piece together, which would add an extra step to the manufacture process.

Breast wrap 101 further comprises means for fastening the panel in a continuous band. Preferably, the panel is wrapped around so that first end 103 is placed on top of second end 105, but this is not limiting to the invention and the second end may be placed on top of the first end with suitable adaptation to the means for fastening. Fastening the panel in a band around a wearer's chest allows the breast wrap to remain in place around the chest without the need for it to be held in place. As a result, the wearer's hands are free to perform other tasks.

Figure 9:
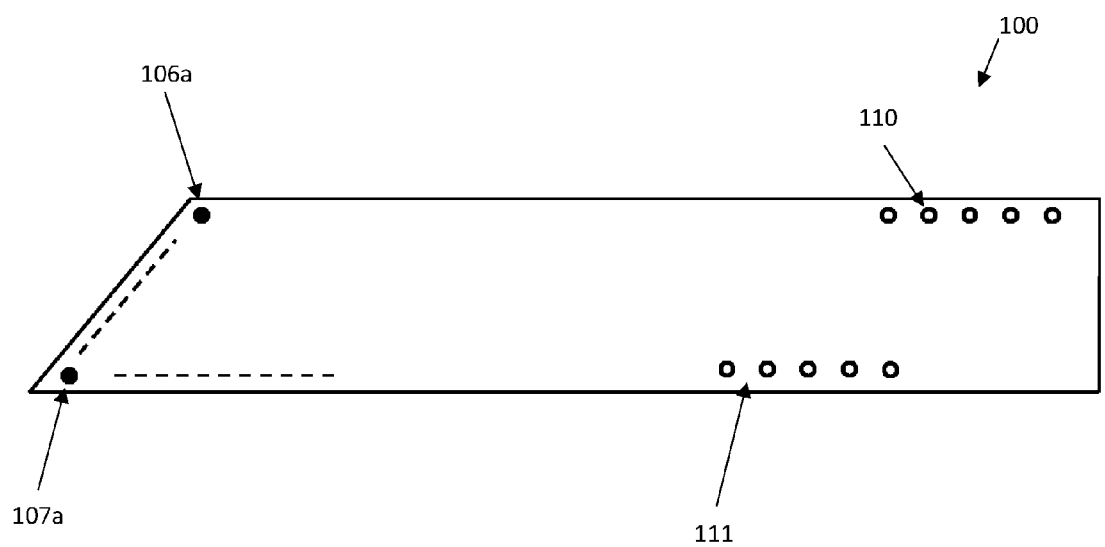
FIG. 9 is a plan view illustration of a breast wrap according to a further embodiment of the invention.

The means for fastening may comprise sets of co-operating fastening members, one of each set being position proximate first end 103 of panel 101 and the other of each set being positioned proximate or near the second end 105 of the panel. In a preferred embodiment, the co-operating fastening members are hook-and-loop fasteners such as VELCRO® hook-and-loop fastening material, sewn on to panel 101. Hook-and-loop fasteners are easy to use and can be easily washed. In addition, they allow for flexibility in the position in which the fasteners can be fixed, which allows for adjustment of the breast wrap. In other embodiments, other types of fasteners are provided such as domes 110, 111 (FIG. 9), poppers, buttons, hooks and eyes and the like.

Advantageously, breast wraps according to the invention are provided with means for adjusting the tightness of the band around the wearer. This allows the breast wrap to be used comfortably by wearers having different sized chests and breasts. A given wearer might find their breasts and body change size following a pregnancy and over the course of breast feeding a child so it is convenient to have a single breast wrap that can cater to their changing body. In preferred embodiments, the breast wrap comprises first and second adjustment means which operate independently to adjust the tightness of the band at two different points or adjustment regions. The adjustment regions may be proximate the top and bottom of the band so that the band can be tightened above and below the wearer's breasts. These two regions of adjustment allow the breast wrap to fit most wearers very comfortably and cater for wearers having different relative sizes of body above and below the breasts. Ensuring the wrap is tightened below the breasts means that the wrap can provide support for the breasts when in use, which further increases the comfort of wearing the wrap.

In some embodiments of the invention, the adjustment means comprise the means for fastening the panel into a band. This makes it simple to use the breast wrap since there is no need to separately fasten and tighten the band.

For example, breast wrap 100 shown in FIG. 1 comprises two sets of co-operating fastening members 106 and 107, each comprising a first fastening member 106*a* and 107*a* proximate the first end 103 of panel 101 and a second fastening member 106*b* and 107*b* near the second end 105. Fastening members 106*a* and 107*a* are positioned on the reverse side of panel 101, i.e. is the side of the panel facing inwards when the wrap is worn, as depicted in FIG. 1 by dotted lines, and fastening members 106*b* and 107*b* are positioned on the outwards facing side of panel 101. In use, first end 103 is placed over second end 105 and the respective co-operating fastening members are fastened together to form the panel into a band around a wearer.

In the embodiment of FIG. 1, fastening member 106*a* is positioned proximate the corner of the panel where the sloped edge 102 of the first end 103 meets the top of the panel, fastening member 106*b* is positioned proximate the top of the panel, proximate the second end 105 of the panel, fastening member 107*a* is positioned proximate the corner of the panel where the sloped edge 102 of the first end 103 meets the bottom of the panel and fastening member 107*b* is positioned proximate the corner of the panel where the taper along the bottom of the panel begins. However, these positions may differ in other embodiments.

As well as enabling the band to be fastened, fastening members 106 and 107 allow adjustment of the tightness of breast wrap 100 when wrapped in a band around the top of the band and bottom of the band respectively. The adjustment is possible because the fastening members may be fastened together in a plurality of positions corresponding to different degrees of tightness of the band. In some embodiments, one or both the fastening members of each set of co-operating fastening members is elongate along the length of the band so that the fastening members may overlap by varying degrees. For example, fastening members 106*b* and 107*b* in FIG. 1 are both elongate. In other embodiments, one or both fastening member of each set may comprise a plurality of individual fastening members. For example, a row of spaced domes 110, 111 (FIG. 9) may be used in place of elongate fastening members 106*b* and 107*b* of FIG. 1.

Some hook-and-loop fasteners, as well as other types of fasteners may be uncomfortable if directly contacting the skin. For example, the "hook" member of VELCRO® hook-and-loop fastening material, can irritate or scratch the skin. As a result, the fastening members are attached in a way to reduce the chances of discomfort. In the embodiment shown in FIG. 1, the "hook" members of the hook-and-loop fasteners are members 106*b* and 107*b* that face away from the body when breast wrap 100 is worn.

Although the adjustment means may comprise the fastening means as has been described in the exemplary embodiment above, in other embodiments they may be provided by separate components. In one embodiment, the fastening means comprises a single set of hook-and-loop fasteners while the adjustment means is provided by one or more draw strings threaded along the top and bottom of the panel of material. Other combinations of fastening means and adjustment means are provided in other embodiments.

In use, the wearer may have taken a bath or shower and started lactating. Having got out of the bath or shower, the wearer wraps the breast wrap around their chest to substantially cover their breasts and fastens it in place. When in place, the breast wrap absorbs any fluid secreted from the wearer's breasts, enabling them to continue with other tasks such as drying themselves, dressing or grooming.

Breast wrap 100 is particularly designed for being wrapped with the centre of panel 101 around the wearer's back and the ends fastened across the front of the body over the breasts because this is a convenient way for the wearer to wrap and fasten the wrap. But breast wrap 100 could be worn in another manner and breast wraps according to other embodiments of the invention may be designed to fasten in other manners.

Fastening breast wrap 100 involves folding first end 103 over the top of second end 105 and joining fastening members 106*a* and 106*b*, and 107*a* and 107*b* together, respectively. Each set of co-operating fastening members is fastened in a manner to ensure optimal comfort, for example the fastening members are positioned to provide the desired tightness and support to the breasts.

In the intended wear position, the first and second adjustment regions of the breast wrap are positioned above and below the wearer's breasts respectively. Adjustment of the breast wrap around the bottom may be found to be particularly important to the fit and comfort of the wrap. The sloped edge 102 of the first end 103 of panel 101 causes the bottom of the first end to extend further than the top. This has been found to be particularly useful for ensuring a good fit and allowing the bottom of the wrap to be fastened more tightly than the top.

After use, the breast wrap can be easily hung up and allowed to dry, just like a towel. It can also be washed like conventional laundry. Breast wraps according to some embodiments of the invention may comprise a hook or other means for conveniently hanging the wrap.

In preferred embodiments of the invention, the breast wrap comprises one or more elastic regions. It will be understood that the term "elastic" is used here in the context of describing any material that has a tendency to resume or return to its original shape after deformation. Examples of such materials are the cords, tapes and fabrics that exhibit elastic behaviour commonly used in clothing. However, the invention envisages that any suitable elastic or elasticated material can be used.

In the embodiment shown in FIG. 1, breast wrap 100 comprises an elastic region 108 along the bottom of panel 101 and an elastic region 109 along sloped edge 102 of the first end 103 of the panel. Other embodiments may have elastic regions in other locations.

Elastic region 108 extends from proximate the extended corner at the first end 103 of the panel to a point approximately one third the distance along the bottom edge of the panel. When the breast wrap 101 is wrapped around a wearer in the intended manner, elastic region 108 is positioned below the wearer's breasts. Elastic region 108 therefore causes the bottom edge of wrap 100 to tighten against the skin of the wearer, which provides a number of advantages. Firstly, it ensures a tight fit of the breast wrap and reduces bagginess. Secondly, holding the wrap against the wearer's skin ensures the wrap can effectively dry the wearer's skin, particularly under the breasts which can be difficult to dry. Thirdly, elastic region 108 provides additional support to the breasts, which many wearers will find increases the comfort of the wrap. Fourthly, elastic region 108 allows the breast wrap 100 to further cater comfortably to wearers of different sizes.

Elastic region 109 extends along the length of the sloped edge 102 of the first end 103 of breast wrap 100 shown in FIG. 1. The presence of elastic region 109 may be desirable to reduce the tendency the breast wrap may have of "gaping" at first end 103 when wrapped around a wearer. Such gaping may be undesirable for being untidy and drafty. Elastic region 109 also allows the breast wrap to cater for wearers of differing breast sizes as the elastic allows sloped edge 102 to conform to the wearer's breast shape. Elastic region 109 additionally provides further breast support because, when fastening members 107a and 107b are joined, elastic region 109 tends to draw the bottom edge of breast wrap 100 upwards.

Other embodiments of the invention include alternative or additional elastic regions. For example, an elastic region may be provided along the top of the breast wrap, which may further increase the adjustability and comfort of the breast wrap.

It will be understood that elastic regions such as those described above may have a tightening effect and therefore provide the breast wrap with the ability to adjust itself to wearers of differing sizes. In some embodiments, the adjustment means may comprise one or more elastic regions such as those described above alone or in combination with other tightness adjusters, such as the fastening members discussed above.

Panel 101 may be made from any suitable material that is able to absorb fluid. Examples of materials that are particularly absorbent are cotton or bamboo terry cloth, velour and towelling material, although any kind of fabric or linen material may be used.

The side of the panel 101 that faces inwards towards the wearer's body in use comprises one or more absorbent regions. At the least, the absorbent region(s) on the panel is/are positioned to cover the wearer's nipples when the wrap is worn and thus absorb fluid secreted therefrom. In the embodiment of FIG. 1, the entire inwards facing side of panel 101 comprises an absorbent material, thus allowing the breast wrap to absorb fluids secreted from the wearer's breasts and to dry water from the wearer's body after a bath, shower of the like.

Panel 101 may comprise one or more layers of material. In one embodiment, panel 101 comprises a first layer of absorbent material, the first layer being on the inner side of the wrap when worn, and a second layer of visually appealing material, the second layer being on the outer side of the wrap when worn. This allows great flexibility in the look of the wrap because the material that can be seen when the wrap is worn is not only limited to the patterns and textures of available absorbent materials. An individual may be able to select their own choice of material for the outer layer or personalise the outer layer in any way, for example by the addition of logos, printed images and the like.

In some embodiments, additional absorbency may be provided in the regions of the wrap that cover a wearer's nipples when in use. This may be desirable for heavily lactating wearers. Additional absorbency in these regions may be achieved by the use of especially absorbent material or extra layers of material. In one embodiment, the breast wrap comprises pockets into which absorbent pads can be inserted to increase the absorbency of the wrap in the regions that cover the wearer's nipples.

In other embodiments, the breast wrap comprises an absorbent panel, or milk absorbing panel(s), that may be attached to the side of the wrap that faces the wearer during use. The absorbent panel may attach to the wrap such that, when the wrap is worn, the absorbent panel is positioned to cover the wearer's nipples and thereby increase the absorbency where it is most needed. In some embodiments, the absorbent panel is attached to the wrap in a removable manner so that it can be washed separately or put aside if not required. The absorbent panel may be removably attached to the breast wrap by means of one or more fastening members, or panel fastener(s), such as hook-and-loop fasteners, domes, poppers, buttons, hooks and eyes and the like.

Figure 3:
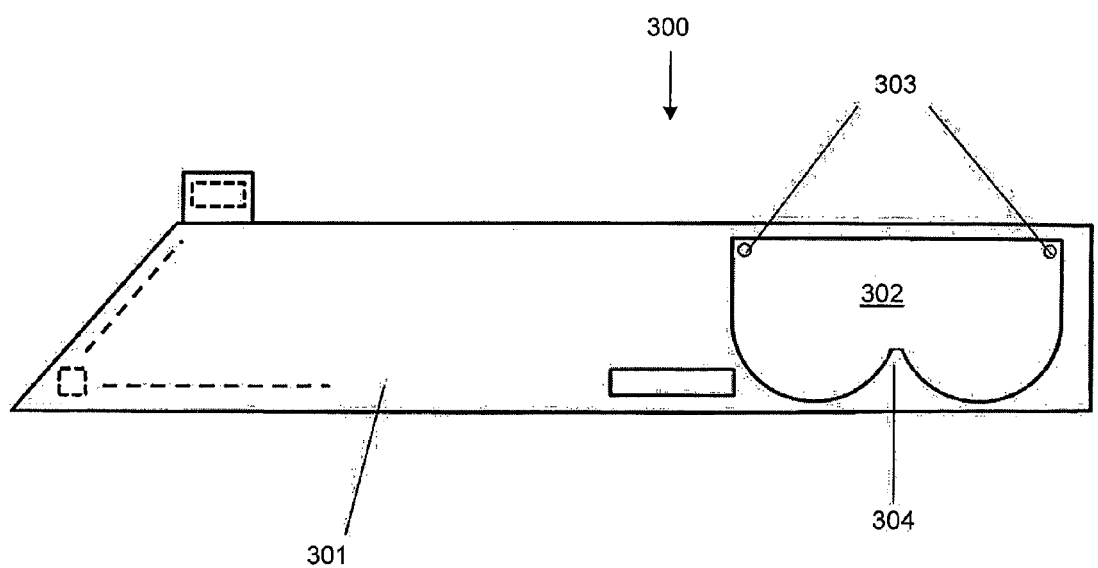
FIG. 3 is a plan view illustration of a breast wrap according to a further embodiment of the invention.

FIG. 3 is a plan view illustration of a breast wrap 300 according to one embodiment of the invention. Breast wrap 300 comprises a panel of material 301, which may be similar to the panel 101 described in relation to the embodiment shown in FIG. 1. Breast wrap 300 additionally comprises an absorbent panel of material(s) 302 which is able to be fastened to panel 301 by means of co-operating portions of fastener sets, or panel fasteners, 303. The absorbent panel 302 is of sufficient size to cover one or more of the wearer's nipples and attaches to the panel 301 at a position suitable to cover said nipples when in use, for example, absorbent panel 302 is substantially similar in width to panel 101 and, when attached thereto, extends from proximate one end of panel 101 across a distance sufficient to cover a woman's chest.

In the embodiment shown in FIG. 3, absorbent panel 302 is shaped along the lower edge to form a central recess 304 in the lower edge of absorbent panel 302. Recess 304 improves comfort to accommodate wearer's of a range of sizes given the differing amounts of stretching of the elastic region along a bottom edge of the panel (such as elastic region 108 of FIG. 1) for users of different sizes. When the elastic region is stretched tightly and fastened under the wearer's breasts, recess 304 allows the sides of the absorbent panel on either side of the recess to move together, preventing bunching together, as would occur if the absorbent panel had a flat bottom edge with no recess, which would create discomfort for the wearer.

Absorbent panel 302 may be made from any suitably absorbent material such as cotton, chamois or bamboo terry cloth, velour or towelling material, or an absorbent microfibre. Multiple layers of material, including layers of more than one material, may be used to increase absorbency compared to using just a single layer.

The absorbent panel 302 may optionally comprise layers of one or more other materials to enhance the comfort or practicality of the breast wrap. For example, a layer of moisture wicking material may be attached to the absorbent material layer(s) on the side of panel 302 that is closest to the wearer's skin, in use. The moisture wicking layer readily transmits moisture through it to the absorbent layer(s) thereby keeping the closest layer to the wearer dry and reducing the discomfort that may be felt by being in contact with damp material. Exemplary moisture wicking materials include microfleece, polar fleece, suedecloth and microchamois. Some hydrophobic materials may also be moisture wicking materials.

The absorbent panel 302 may further comprise a waterproof layer positioned on the side of the panel furthest from the wearer when in use, i.e. behind the layer(s) of absorbent material. This layer helps to trap absorbed moisture within the layer(s) of absorbent material, thus helping to prevent moisture leaking out, for example, onto bedsheets when the wrap is worn in bed. Any waterproof fabric may be used such as polyurethane laminated polyester (PUL), which has the advantage of having a soft side that can face outwards and be comfortable to touch, other laminated materials or nylon.

Figure 10:
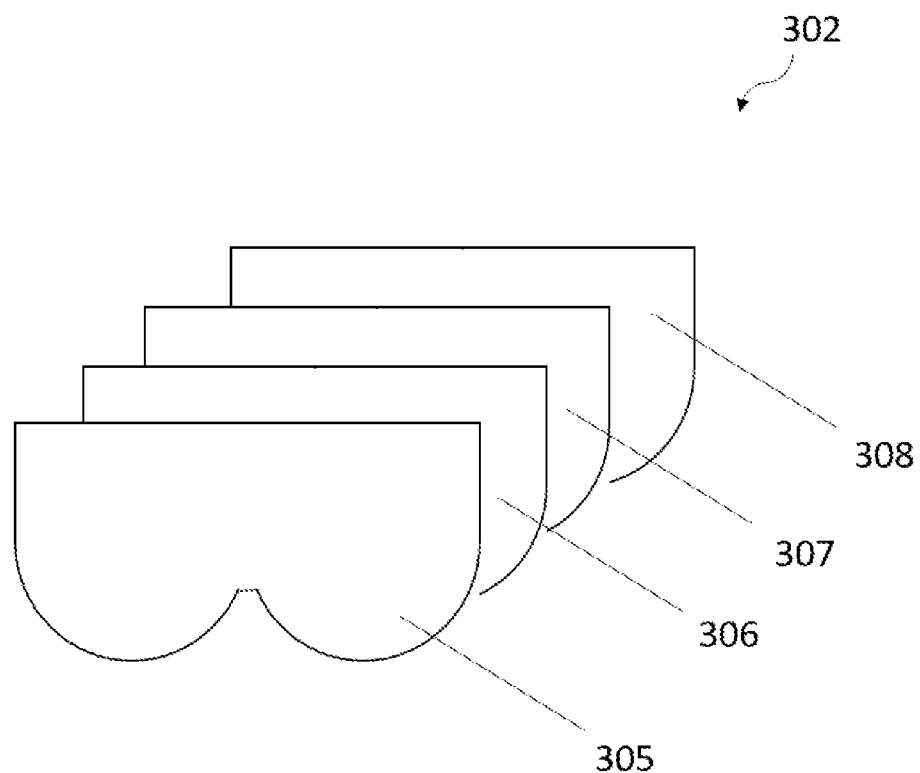
FIG. 10 is an exploded view illustration of an absorbent panel for use with the breast pad of the present invention.

In one particular embodiment as shown in FIG. 10, the absorbent panel comprises four layers of material as follows in order of closest to the wearer to furthest from the wearer when in use: a moisture wicking layer 3055 formed from microfleece; a first absorbent layer 306 formed from an absorbent microfibre; a second absorbent layer 307 formed from bamboo towelling; and a waterproof layer 308 from PUL. The ordering of the first and second absorbent layers in this embodiment may be desirable because microfibre absorbs moisture more quickly than bamboo towelling so serves to quickly take wetness away from the wearer's body and the bamboo layer subsequently absorbs this moisture more slowly.

It will be apparent that the layers of material used in the absorbent panel may be attached together in any suitable manner, for example by sewing them together. In one preferred embodiment the layers are sewn together and bound using bias binding or any other suitable binding technique.

Figure 2:
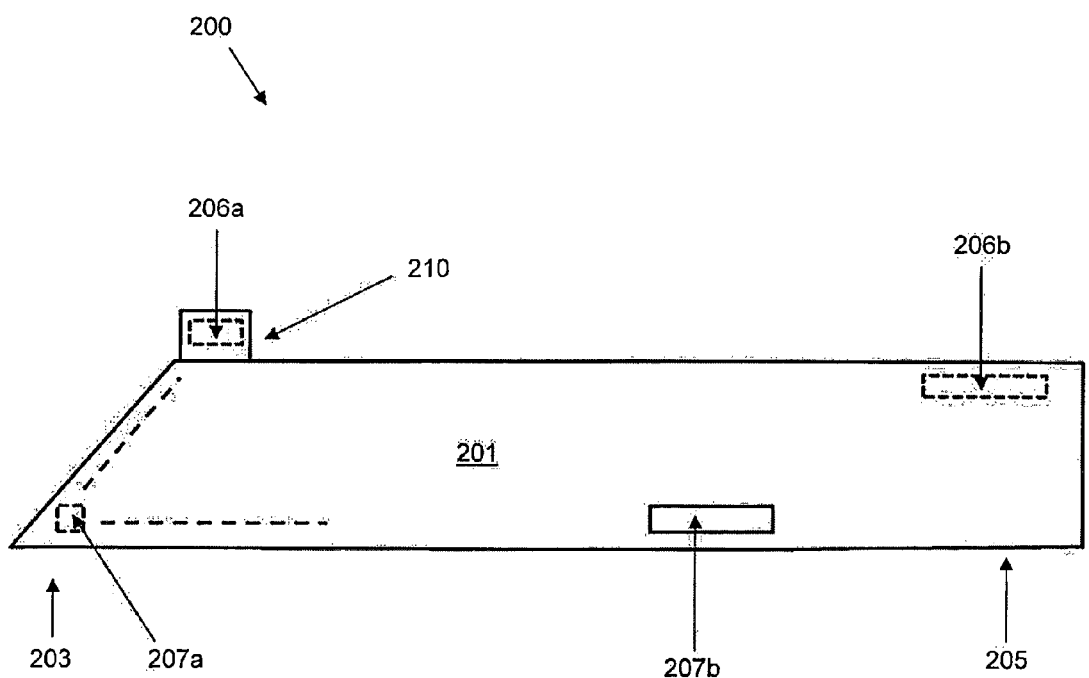
FIG. 2 is a plan view illustration of a breast wrap according to another embodiment of the invention.

FIG. 2 is a plan view illustration of a breast wrap 200 according to another embodiment of the invention. Breast wrap 200 is similar in many respects to breast wrap 100 of FIG. 1. Only those features of breast wrap 200 that differ from breast wrap 100 will now be described.

Breast wrap 200 comprises a flap of material 210 extending out from the top edge of panel 201 proximate first end 203. Fastening member 206a is attached to the reverse side of flap 210, as depicted by the dotted line in FIG. 2. Fastening member 206b at the second end 205 of panel 201 (with which fastening member 206a fastens to secure the panel into a band) is also attached to the reverse side of the panel. To secure the panel into a band, flap 210 is folded over the top edge of the second end 205 of panel 201 whereupon fastening members 206a and 206b can be fastened together.

When breast wrap 100 shown in FIG. 1 is wrapped around a wearer, because fastening member 106b is elongate, some part of fastening member 106b may be visible from the front unless fastening member 106a is attached to fastening member 106b in the tightest possible configuration. The visibility of some part of fastening member 106b may be undesirable. Breast wrap 200 as shown in FIG. 2 avoids this scenario because fastening member 206b is attached to the reverse side of the breast wrap.

In other embodiments of the invention, one or more other flaps may be provided in a similar manner to flap 210 to render the fasteners invisible, as desired.

FIGS. 4 to 8 are illustrations of a breast wrap 400 being wrapped and fastened by a wearer 401 according to one embodiment of the invention. Breast wrap 400 is similar to the breast wrap 200 described in relation to FIG. 2 as it has a flap 410 similar to flap 210 of FIG. 2.

Figure 4:
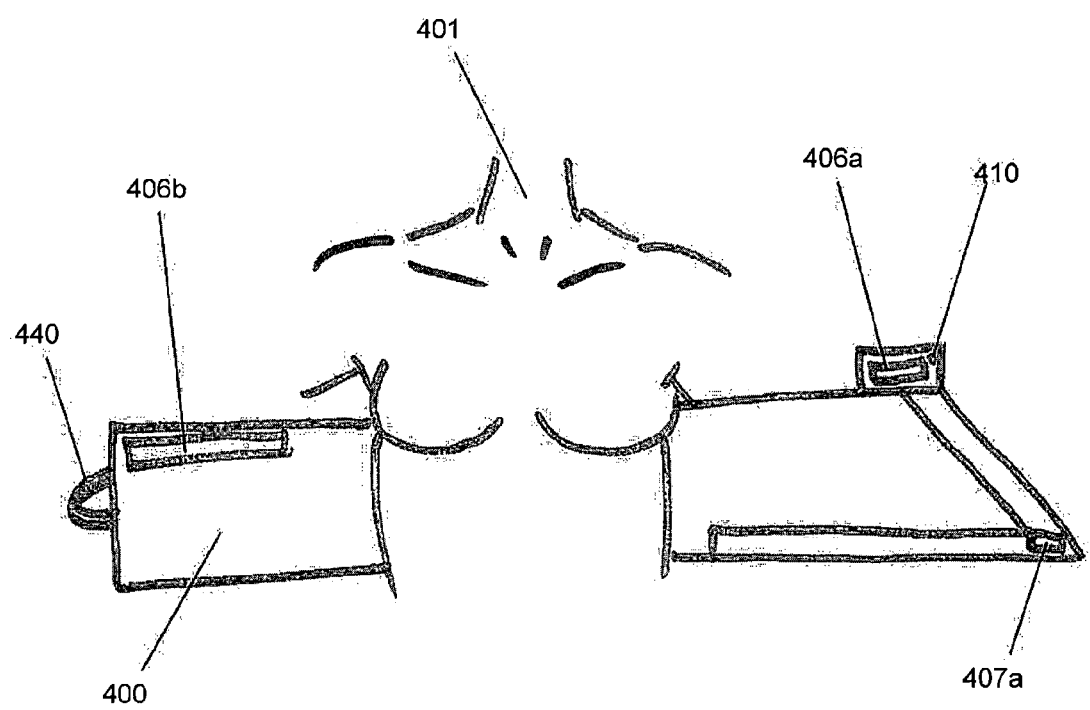
FIGS. 4-8 are illustrations of a breast wrap being wrapped and fastened by a wearer according to one embodiment of the invention.

Firstly, as shown in FIG. 4, the wrap is held behind the back with flap 410 at the top and fastening members 406a, 406b and 407a facing inwards towards the wearer. Reference numerals in relation to FIGS. 4-8 refer to similar features as described in relation to FIG. 2, but with the prefix "4" instead of "2".

Figure 5:
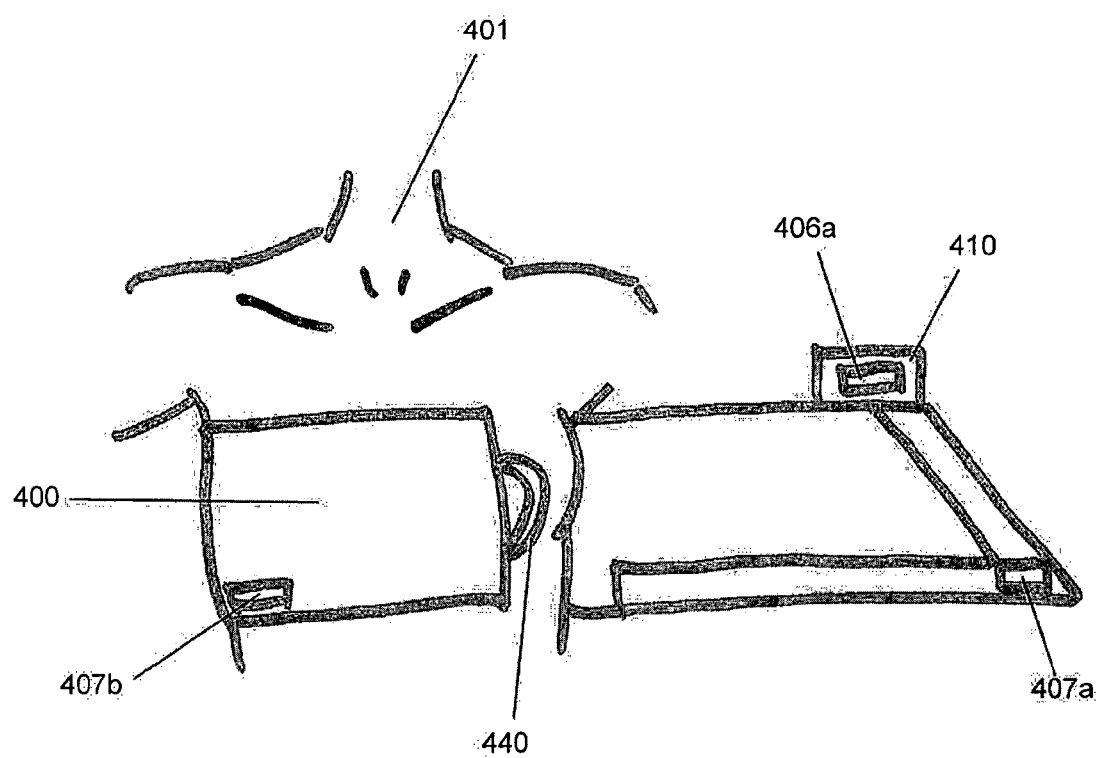

Next, as shown in FIG. 5, one end of the wrap is folded across the wearer's chest to cover the nipples and in particular, if an extra absorbent layer is present, so that the absorbent layer covers the nipples. In the embodiment shown, the end opposite to the end with the flap 410 on it is folded across the chest. A loop 440 may be attached to this end, which may be used to hang up the wrap when not in use.

Figure 6:
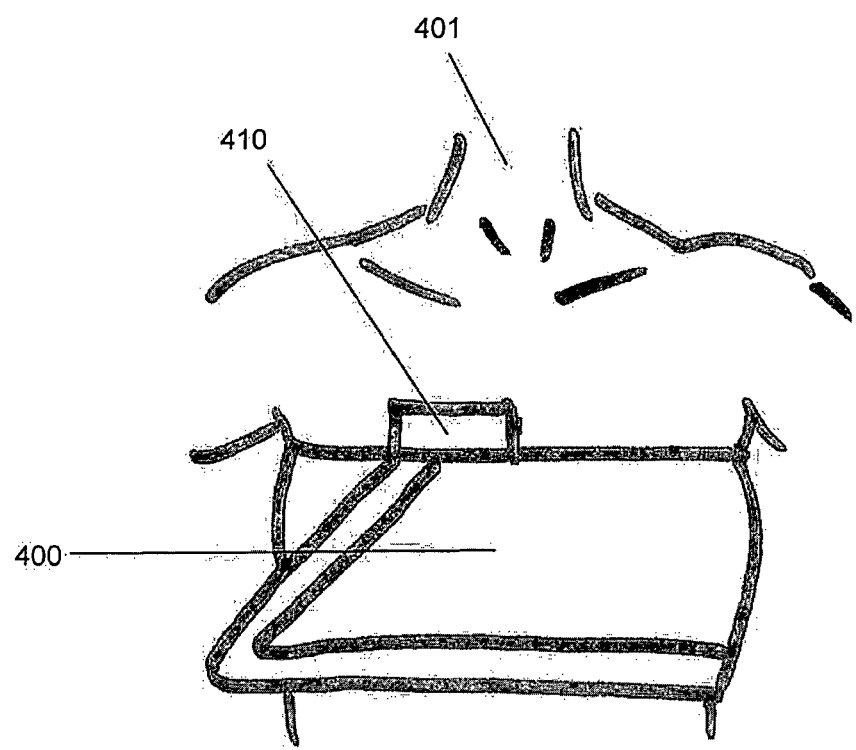

In the next step, as shown in FIG. 6, the other end of the wrap is folded across the wearer's chest on top of the end already folded across the chest.

Figure 7:
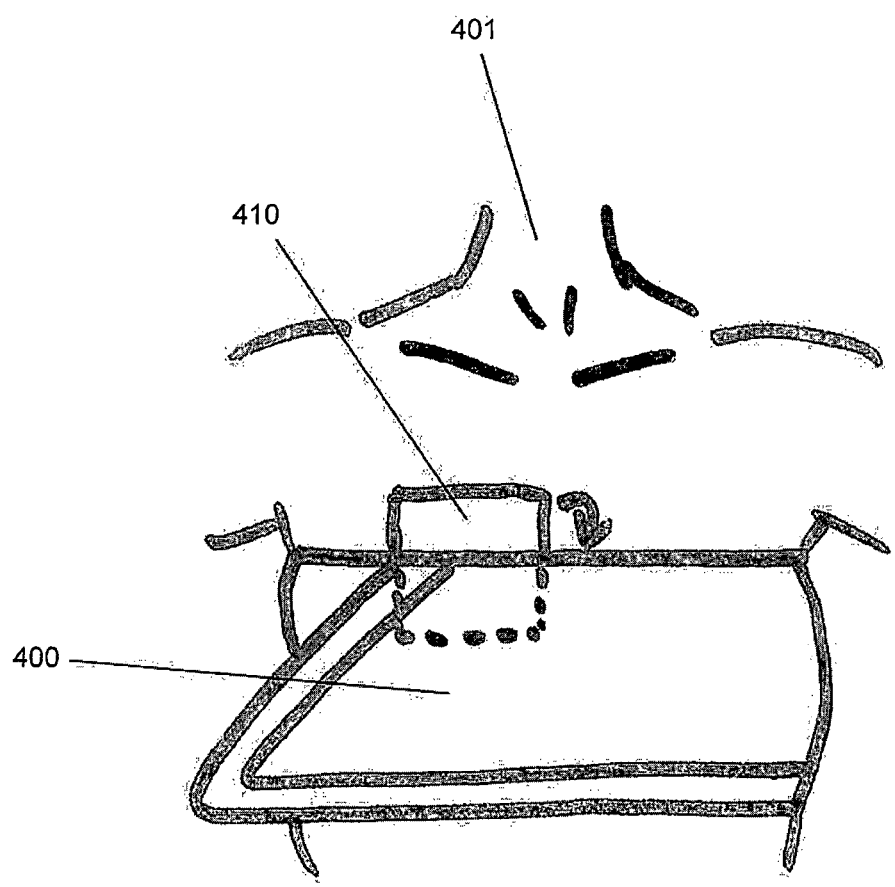

Next, as shown in FIG. 7, the flap 410 is folded towards the wearer's body over the inner layer of the wrap and the fastening member 406a on the flap is fastened to fastening member 406b on the inside of the inner layer.

Figure 8:
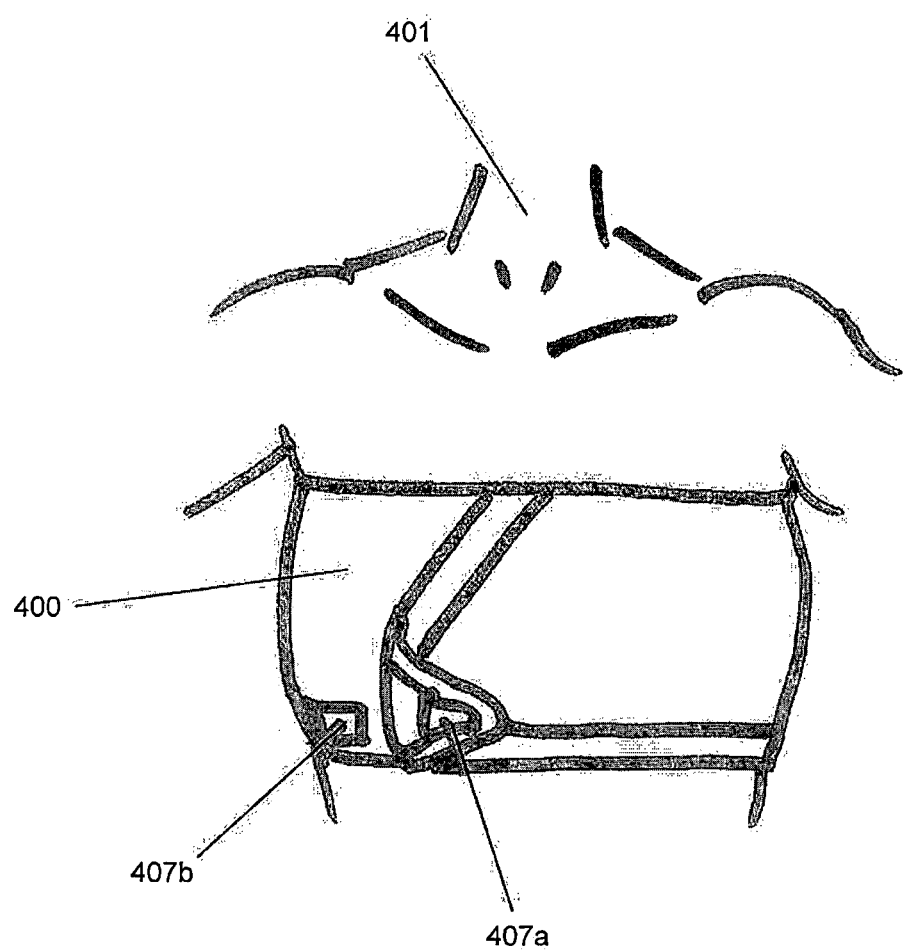

Finally, as shown in FIG. 8, the bottom corner of the wrap is pulled across the chest and the fastening members 407a and 407b are fastened together so as to hold the wrap in place and optionally to support the wearer's breasts, as has previously been described.

Numerous advantages of the invention and its embodiments have been described above. Other advantages over prior breast wraps may also be evident to the skilled addressee. Examples of further advantages are that the comfort of breast wraps according to the invention mean they may be kept on for extended period of time, for example for sitting around the house or sleeping. The invention has the advantage over some prior art absorbent garments in that there are no straps for wearing over the shoulders. Straps can dig in to the wearer uncomfortably and also increase the complexity of putting the garment on.

Breast wraps according to the invention may have absorbent material forming both the wrap itself and comprising the removable absorbent layer that can be fastened to the wrap to provide further absorbency. This gives the user the advantage of being able to remove the extra absorbency layer for washing once it is moisture-laden, for example after use at night, then still use the wrap again, for example following a shower, to absorb lower levels of milk without the extra absorbency layer.

Further removable absorbency layers may also be provided to provide extra absorbency while the first absorbent layer is unavailable, for example being washed.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. In particular, construction of the breast wrap of the present invention may incorporate any number of known sewing techniques such as the use of bindings, facings, darts, pleats or linings for example. Such changes and modifications may be made without departing from the spirit and scope of the invention and without diminishing its attendant advantages. It is therefore intended that such changes and modifications be included within the present invention.

The invention claimed is:

1. A lactation breast wrap for absorbing milk secreted from nipples of breasts of a wearer, the lactation breast wrap comprising:
    a panel of material having a first end and a second end separated by a length, and having a top and bottom separated by a height, wherein the length of the panel is greater than the height of the panel;
    one or more fasteners for fastening the panel in a continuous band when the panel is wrapped around so that the first end overlaps with the second end, the band having a top, wherein the top of the band is formed by the top of the panel and has a top circumference, and the band having a bottom, wherein the bottom of the band is formed by the bottom of the panel and has a bottom circumference,
    wherein the first end of the panel comprises a sloped edge, the sloped edge extending from the top of the panel to the bottom of the panel, wherein the bottom of the panel is longer than the top of the panel when the panel is not wrapped around to form the band; and
    one or more milk absorbing regions on a first side of the panel, the one or more milk absorbing regions for absorbing milk secreted from the nipples of the wearer; and
    said one or more fasteners including first and second fasteners independently operable so that, when the panel forms the band, the first fasteners enable adjustment of the top circumference of the band that the second fasteners enable adjustment of the bottom circumference of the band; and
    an elastic region along the bottom of the panel positioned so that, in use, the elastic region along the bottom of the panel is positioned below the breasts of the wearer at the front of the wearer, and an elastic region along an edge of the panel at the first end, the elastic region along the edge of the panel at the first end acting to draw the bottom of the panel towards the top of the panel at the first end of the panel to, in use, provide support to the breasts of the wearer;
    wherein, in use, the wrap is configured to wrap around the chest of the wearer and substantially cover the breasts of the wearer with the one or more milk absorbing regions covering the nipples of the wearer, the top of the band positioned above the breasts of the wearer and the bottom of the band positioned below the breasts of the wearer, and
    wherein the wrap is free of straps for wearing over the shoulder of the wearer in use.

2. A lactation breast wrap as claimed in claim 1, wherein the first fasteners comprise: a top set of co-operating fastening members positioned proximate the top of the panel; and the second fasteners comprise a bottom set of co-operating fastening members positioned proximate the bottom of the panel.

3. A lactation breast wrap as claimed in claim 2, wherein each of the sets of first fastening members and the second fastening members are able to fasten together in different configurations when the panel forms the band, thereby allowing the top circumference of the band and the bottom circumference of the band to be independently adjusted.

4. A lactation breast wrap as claimed in claim 1, wherein the elastic region along the first end is along the sloped edge of the first end of the panel.

5. A lactation breast wrap as claimed in claim 1, wherein the wrap comprises:
    one or more first panel fasteners, the first panel fasteners on a wearer-facing side of the panel; and
    one or more milk absorbing panels for absorbing milk secreted from the nipples of the wearer, wherein each of the one or more milk absorbing panels comprises one or more second panel fasteners, each of the second panel fasteners being configured to fasten to a respective one of the first panel fasteners to removably attach the respective milk absorbing panel to the wearer-facing side of the panel at a predetermined position.

6. A lactation breast wrap for absorbing milk secreted from nipples of breasts of a wearer, the lactation breast wrap comprising:
    a first panel of material having a first end and a second end separated by a length, and having a top and bottom separated by a height, wherein the length of the panel is greater than the height of the panel and wherein the height of the panel is substantially constant along the length of the panel;
    one or more band fasteners for fastening the first panel in a continuous band and wherein the first end of the panel comprises a sloped edge extending from the top of the panel to the bottom of the panel, wherein the bottom of the panel is longer than the top of the panel;
    an elastic region along the first end of the panel and an elastic region along the bottom edge of the panel positioned so that, in use, the elastic region along the bottom of the panel is positioned below the breasts of the wearer at the front of the wearer, the elastic region along the first end of the panel acting in use to draw the bottom of the panel towards the top of the panel;
    one or more first panel fasteners, the first panel fasteners on a first side of the panel; and
    one or more absorbing panels for absorbing milk secreted from the nipples of the wearer, each of the one or more absorbing panels comprises one or more second panel fasteners on a wearer-facing side of the first panel, each of the second panel fasteners being configured to fasten a respective one of the first panel fasteners to removably attach the respective absorbing panel to a wearer-facing side of the first panel at a predetermined position, and each of the one or more absorbing panels having a central recess along a lower edge of the absorbing panel,
    wherein, in use, the wrap is configured to wrap around a chest of the wearer and substantially cover the breasts of the wearer with the one or more milk absorbing panels covering the nipples of the wearer,
    wherein the one or more milk absorbing panels comprise at least one layer of milk absorbing material and at least one layer of waterproof or water resistant material, the at least one layer of waterproof or water resistant material being positioned further from the chest of the wearer than the at least one layer of milk absorbing material when in use, and wherein the wrap is free of straps for wearing over shoulders of the wearer in use.

7. The lactation breast wrap of claim 6, wherein the at least one layer of milk absorbing material comprises at least one material selected from the group consisting of: cotton, chamois or bamboo terry cloth, velour or toweling material, and an absorbent microfiber.

8. The lactation breast wrap of claim 6, wherein the one or more milk absorbing panels each comprise a layer of moisture wicking material.

9. A lactation breast wrap for absorbing milk secreted from nipples of breasts of a wearer, the lactation breast wrap comprising:
  a panel of material having a first end and a second end separated by a length, and having a top and bottom separated by a height, wherein the length of the panel is greater than the height of the panel, wherein the first end of the panel has a sloped edge extending from the top of the panel to the bottom of the panel, and wherein the bottom of the panel is longer than the top of the panel;
  an elastic region along the sloped edge of the first end of the panel and an elastic region along the bottom of panel positioned so that, in use, the elastic region along the bottom of the panel is positioned below the breasts of the wearer at the front of the wearer, the elastic region along the sloped edge of the first end of the panel acting to draw the bottom of the panel towards the top of the panel at the first end of the panel;
  one or more fasteners for fastening the panel in a continuous band when the panel is wrapped around so that the first end overlaps with the second end, the band having a top, wherein the top of the band is formed by the top of the panel and has a top circumference, and the band having a bottom, wherein the bottom of the band is formed by the bottom of the panel and has a bottom circumference,
  one or more milk absorbing regions on a wearer-facing side of the panel, the one or more milk absorbing regions for absorbing milk secreted from the nipples of the wearer;
  and
  said one or more fasteners including first and second fasteners independently operable so that, when the panel forms the band, the first fasteners enable adjustment of the top circumference of the band that the second fasteners enable adjustment of the bottom circumference of the band,
  wherein the wrap is free of straps for wearing over the shoulder of the wearer in use, and
    wherein, in use, the wrap is configured to wrap around the chest of the wearer and substantially cover the breasts of the wearer with the one or more milk absorbing regions covering the nipples of the wearer, the top of the band positioned above the breasts of the wearer and the bottom of the band positioned below the breasts of the wearer.

* * * * *